(12) United States Patent
Jung et al.

(10) Patent No.: US 8,993,268 B2
(45) Date of Patent: Mar. 31, 2015

(54) **METHOD OF PRODUCING *CLOSTRIDIUM BOTULINUM* TOXIN USING MEDIA CONTAINING PLANT-DERIVED COMPONENTS AND FLEXIBLE CLOSED CONTAINER**

(75) Inventors: Hyun-Ho Jung, Seoul (KR); Gi-Hyeok Yang, Chungcheongnam-Do (KR); Hack-Woo Kim, Chungcheongbuk-Do (KR); Byung-Kook Lee, Seoul (KR); Young-suk Yoon, Chungcheongbuk-Do (KR); Hyung-Pyo Hong, Chungcheongbuk-Do (KR)

(73) Assignee: Medy-Tox Inc. (KR)

( * ) Notice: Subject to any disclaimer, the term of this patent is extended or adjusted under 35 U.S.C. 154(b) by 81 days.

(21) Appl. No.: 12/993,332

(22) PCT Filed: Jul. 2, 2008

(86) PCT No.: PCT/KR2008/003897
§ 371 (c)(1),
(2), (4) Date: Nov. 18, 2010

(87) PCT Pub. No.: WO2009/142352
PCT Pub. Date: Nov. 26, 2009

(65) Prior Publication Data
US 2011/0091937 A1    Apr. 21, 2011

(30) Foreign Application Priority Data
May 19, 2008    (KR) .................. 10-2008-0046152

(51) Int. Cl.
*C12P 21/04*    (2006.01)
*C07K 14/33*    (2006.01)
*C12N 1/20*    (2006.01)
*C12N 9/52*    (2006.01)

(52) U.S. Cl.
CPC . *C07K 14/33* (2013.01); *C12N 1/20* (2013.01); *C12Y 304/24069* (2013.01); *C12N 9/52* (2013.01)
USPC ........................................ 435/71.3; 435/71.1

(58) Field of Classification Search
USPC ............................... 435/71.3, 71.1
See application file for complete search history.

(56) References Cited

U.S. PATENT DOCUMENTS

| 5,846,929 | A | * | 12/1998 | Johnson et al. | ............. | 435/68.1 |
| 6,190,913 | B1 | * | 2/2001 | Singh | ............ | 435/394 |
| 6,544,788 | B2 | | 4/2003 | Singh | | |
| 6,673,598 | B1 | | 1/2004 | Akers et al. | | |
| 2005/0238668 | A1 | * | 10/2005 | Wang et al. | ............. | 424/239.1 |
| 2006/0240514 | A1 | * | 10/2006 | Donovan | ............ | 435/69.1 |
| 2006/0269575 | A1 | * | 11/2006 | Hunt | ............ | 424/239.1 |

FOREIGN PATENT DOCUMENTS

WO    00/66706    11/2000
WO    2006/096163    9/2006

OTHER PUBLICATIONS

International Search Report dated Feb. 18, 2009 for International Application No. PCT/KR2008/003897 (English).
ATCC Deposition No. 3502 (deposit record), "*Clostridium botulinum* (van Ermengen) Bwergey et al.," 1 page.
Binz et al. (Jun. 1990) "The Complete Sequence of Botulinum Neurotoxin Type A and Comparison with Other CLostridial Neurotoxins," J. Biol. Chem. 265(16):9153-9158.
Montecucco et al. (Sep. 1993) "Tetanus and Botulism Neurotoxins: a New Group of Zinc Proteases," TIBS 18:324-327.
Park et al. (1990) "Binding of *Clostridium botulinum* Type B Toxin to Rat Brain Synaptosome," FEMS Microbiol.Lett. 72:243-248.
Poulain et al. (1988) "Neurotransmitter Release is Blocked Intracellularly by Botulinum Neurotoxin, and This Requires Uptake of Both Toxin Polypeptides by a Process Mediated by the Larger Chain," Proc. Natl. Acad. Sci. USA. 85:4090-4094.
Schant et al. (Mar. 1992) "Properties and Use of Botulinum Toxin and Other Microbial Neurotoxins in Medicine," Microbiol. Rev. 56(1):80-99.
Simpson, L.L. (1986) "Molecular Pharmacology of Botulinum Toxin and Tetanus Toxin," Ann. Rev. Pharmacol. Toxicol. 26:427-453.
Singh (1996) Critical Aspects of Bacterial protein Toxins, Natural toxins II, edited by B.R. Signh et al., Plenum Press, New York, pp. 63-84.
Sugiyama, H. (Sep. 1980) "*Clostridium botulinum* Neurotoxin," Microbiol. Rev. 44(3):419-448.
Extended European search report EP13 19 0331, Apr. 23, 2014.
Supplementary European Search Report, dated Apr. 8, 2013, corresponding to International Application No. PCT/KR2008/003897 (filed Jul. 2, 2008), parent of the present application, 9 pp.
Demain et al. (2007) "Tetanus Toxin Production in Soy-Based Medium: Nutritional Studies and Scale-Up Into Small Fermentors," Letters in Applied Microbiology 45:635-638.

\* cited by examiner

*Primary Examiner* — Karen Cochrane Carlson
*Assistant Examiner* — Natalie Moss
(74) *Attorney, Agent, or Firm* — Ted A. Chan; Debra D. Condino

(57) ABSTRACT

Provided are a method of producing *Clostridium botulinum* toxin by using a media containing plant-derived components, and a method of producing *Clostridium botulinum* toxin by using a flexible closed container.

10 Claims, No Drawings

METHOD OF PRODUCING *CLOSTRIDIUM BOTULINUM* TOXIN USING MEDIA CONTAINING PLANT-DERIVED COMPONENTS AND FLEXIBLE CLOSED CONTAINER

CROSS-REFERENCE TO RELATED APPLICATIONS

This application is the U.S. National Stage of International Application No. PCT/KR2008/003897, filed Jul. 2, 2008, which claims the benefit of Korean Patent Application No. 10-2008-0046152, filed May 19, 2008, both of which are hereby incorporated by reference to the extent not inconsistent with the disclosure herewith.

TECHNICAL FIELD

This application claims the benefit of Korean Patent Application No. 10-2008-0046152, filed on May 19, 2008, in the Korean Intellectual Property Office, the disclosure of which is incorporated herein in its entirety by reference.

The present invention relates to a method of producing *Clostridium botulinum* toxin using a media containing plant-derived components and a flexible closed container.

BACKGROUND ART

*Clostridium* strains, which produce toxin with neurotoxicity, have been found since 1890 up to present, and research into the properties of toxin produced by *Clostridium* strains has been conducted for 70 years (Schant, E. J. et al, Microbiol. Rev. 56; 80; 1992).

The genus *Clostridium* has more than 127 species, and is grouped according to their morphology and functions. Anaerobic and Gram-positive bacteria *Clostridium botulinum* produces a polypeptide neurotoxin that causes neural paralysis, which is referred to as botulism, in humans and animals. Spores of *Clostridium botulinum* are found in soil, and a large amount thereof can be germinated and cultured even in not fully processed foods. These can be causes of botulism.

*Botulinum* toxin is divided into seven types A through G according to their serological characteristics. Each toxin has about 150 kDa of toxin protein, and naturally comprises a complex with a variety of non-toxic proteins bound thereto. An intermediate complex (300 kDa) comprises toxin protein and non-toxic non-hemaglutinin protein, and a large complex (500 kDa) and a macro complex (900 kDa), each has a structure in which the intermediate complex is bound to hemaglutinin (Sugiyama, H., Microbiol. Rev., 44, 419; 1980). Such a non-toxic non-hemaglutinin protein is known to protect a toxin from a low pH of intestines, and various kind of protein hydrolytic enzymes (Sugiyama, H., Microbiol. Rev., 44, 419; 1980).

*Botulinum* toxin is synthesized in a cell, as a single-chain polypeptide, with a molecular weight of approximately 150 kDa, and then cleaved into two subunits at a position that is one-third the distance from an N-terminal by using protease in the cell or by using an artificial enzyme treatment such as trypsin: a light chain with a molecular weight of 50 kDa and a heavy chain with a molecular weight of 100 kDa. Such toxin cleaved into two subunits has highly increased toxicity in comparison with the single-chain polypeptide. The two subunits are bound to each other by a disulfide bond, and each subunit differently functions. That is, the heavy chain binds with a receptor of a target cell (FEMS Microbiol. Lett. 72, 243; 1990), and reacts with a bio-membrane at a low pH (pH 4.0) to form a channel (Mantecucco, C. et al, TIBS 18, 324; 1993). On the other hand, the light chain has pharmacological activities, and thus when the light chain is introduced into the cell by electroporation or enhanced permeability caused by a surfactant, the light chain interferes with secretion of a neurotransmitter (Poulain, B. et al, Proc. Natl. Acad. Sci. USA. 85, 4090; 1988).

*Botulinum* toxin type A is the most lethal natural biological agent known to man. On a molar basis, *Botulinum* toxin type A is 1.8 billion times more lethal than diphtheria toxin, 600 million times more lethal than sodium cyanide, 30 million times more lethal than cobratoxin and 12 million times more lethal than cholera toxin (Singh, Critical Aspects of Bacterial protein Toxins, page 63-84 of natural toxins II, edited by B. R. Sigh et al., Plenum Press, New York (1976)).

*Botulinum* toxin inhibits exocytosis of acetylcholine from a cell at a cholinergic presynapse of a neuromuscular junction, thereby causing asthenia. Taking into account that in spite of the treatment of a very small amount of *Botulinum* toxin, toxicity is exhibited, it is considered that *Botulinum* toxin may have an enzyme activity (Simpson, L. L. et al, Ann. Rev. Pharmaeol. Toxicol. 26, 427; 1986). According to recent reports, *Botulinum* toxin has a metallopeptidase activity, and a substrate thereof is unit proteins of an exocytosis machinery complex, such as synaptobrevin, syntaxin, and synaptosomal associated protein of 25 kDa (SNAP 25). Each type of *Botulinum* toxin uses one of the three proteins as a substrate, and it is known that *Botulinum* toxin type B, D, F, and G cleave synaptobrevin at a specific site, *Botulinum* toxin type A and E cleave SNAP25 at a specific site, and *Botulinum* toxin type C cleaves syntaxin at a specific site (Binz, T. et al, J. Biol. Chem. 265, 9153; 1994).

WO06/096163 discloses that a seed culture and a main culture are performed under nitrogen, and the pH is adjusted from 5 to 5.5 in order to express *Botulinum* toxin protein. In addition, multi-step chromatography is performed, and washing and sterilization must be performed using reusable equipment and consumables. Such a system requires many labor and high investment costs, and high risk factors exist in the system in order to meet cGMP (current good manufacturing practice) requirements.

DISCLOSURE OF INVENTION

Technical Problem

Therefore, the inventors of the present application found that a large amount of *Clostridium botulinum* toxin was expressed outside the cell by using a composition of plant-derived components, and *Clostridium botulinum* toxin could be effectively produced by using a disposable bioreactor through fermentation that used strict anaerobes, *Clostridium botulinum* strains. In addition, the inventors of the present application found that *Clostridium botulinum* toxin could be easily and very simply purified from the culture from which the cell was removed. Thus, the present invention was completed.

The present invention provides a method of producing *Clostridium botulinum* toxin using a media containing plant-derived components.

The present invention also provides a method of producing *Clostridium botulinum* toxin using a flexible closed container.

Technical Solution

The present invention provides a method of producing *Clostridium botulinum* toxin, the method including: (a) culturing *Clostridium botulinum* in a media containing plant-derived components to express *Clostridium botulinum* toxin outside a cell; and (b) removing the cell from the obtained culture to obtain a portion including *Clostridium botulinum* toxin expressed outside the cell and isolating the *Clostridium botulinum* toxin from the portion.

In the method of present invention, *Clostridium botulinum* is cultured in the media containing plant-derived components to express *Clostridium botulinum* toxin outside the cell (operation (a)). In the present operation, culturing is performed using the media containing plant-derived components, thereby expressing a toxin outside the cell, unlike the prior art. The expression 'express *Clostridium botulinum* toxin outside the cell' used herein indicates that after the cell produces the toxin therein, not only does the cell transport the toxin outside the cell spontaneously, but the cell containing the toxin expressed in the cell is also lysed whereby the toxin is exposed in a solution of the culture, not in the cell of the culture.

The media containing plant-derived components may comprise phytone peptone, and preferably, phytone peptone, yeast extract, and glucose. In addition, the media containing plant-derived components may further comprise at least one component selected from the group consisting of vegetable tryptone, soytone, and sodium thioglycolate. In an embodiment, the media containing plant-derived components may be one selected from the group consisting of a media comprising glucose, yeast extract, and phytone peptone; a media comprising glucose, yeast extract, phytone peptone, and vegetable tryptone; a media comprising glucose, yeast extract, phytone peptone, and soytone; a media comprising glucose, yeast extract, soytone, and vegetable tryptone; a media comprising glucose, yeast extract, sodium thioglycolate, phytone peptone, vegetable tryptone, and soytone; and a media comprising glucose, yeast extract, phytone peptone, vegetable tryptone, and soytone.

In another embodiment, the amounts of glucose, yeast extract, sodium thioglycolate, phytone peptone, vegetable tryptone, and soytone in each media described above may be 0.2 wt % to 2 wt %, 0.5 wt % to 3 wt %, 0.05 wt % to 2 wt %, 0.5 wt % to 2 wt %, 0.5 wt % to 2 wt %, and 0.5 wt % to 2 wt %, respectively, based on total weight of the media. In another embodiment, the media containing plant-derived components may be one selected from the group consisting of a media comprising glucose, yeast extract, and phytone peptone; a media comprising glucose, yeast extract, phytone peptone, and vegetable tryptone; a media comprising glucose, yeast extract, phytone peptone, and soytone; a media comprising glucose, yeast extract, soytone, and vegetable tryptone; a media comprising glucose, yeast extract, sodium thioglycolate, phytone peptone, vegetable tryptone, and soytone; and a media comprising glucose, yeast extract, phytone peptone, vegetable tryptone, and soytone. In this regard, the amounts of glucose, yeast extract, sodium thioglycolate, phytone peptone, vegetable tryptone, and soytone in each media described above are 0.2 wt % to 2 wt %, 0.5 wt % to 3 wt %, 0.05 wt % to 2 wt %, 0.5 wt % to 2 wt %, 0.5 wt % to 2 wt %, and 0.5 wt % to 2 wt %, respectively, based on total weight of the media, and the rest of the media may comprise water.

The *Clostridium botulinum* toxin may be one selected from the group consisting of *botulinum* toxin A, B, C, D, E, F, and G, and preferably, *botulinum* toxin A.

In operation (a), the culturing may be performed by introducing a culture media in a closed container including an inlet and an outlet and comprised of a flexible material, inoculating the culture media with *Clostridium botulinum*, and culturing the cell. The closed container is well-known in the art related to animal cell culture and commercially available (for example, Cultibag™, manufactured by Wave Biotech). For example, the closed container may be a closed container disclosed in WO00/66706, but the present invention is not limited thereto. The closed container is pre-sterilized, and may be in a bag form, for example, in a plastic bag form. When the closed container is empty, the container is in the form of a sheet that consists of two closely aligned layers of flexible materials, thereby has no substantial inner space volume. When a sample such as a medium or a cell solution is introduced through the inlet, a space between the two layers of the flexible materials is formed to accommodate the sample without any substantial introduction air.

The closed container may be stirred utilizing rocking motion. The culture media in the closed container mounted on a platform of a rocker may be stirred utilizing rocking motion. The rocker rocks the platform around an oscillation axis. The rocker is well-known in the art related to animal cell culture, and can be purchased as a part of Cultibag™ (Wave Biotech or Sartorius). The closed container is air-impermeable, and thus the inside thereof can be maintained in a condition that oxygen is not able to be provided from the outside, from when the culture media is introduced in the closed container, and the culture media is inoculated with *Clostridium botulinum*, to when the culturing of the cell is completed.

Thus, the culturing may be performed without supplying nitrogen, without using a chemical material having an oxygen removal activity (for example, sodium thioglycolate), or without adjustment of pH in order to maintain anaerobic conditions. The culturing may be performed under conditions of stirring by the rocking motion of a rocker, or may be performed under no stirring conditions.

In the method of the present invention, the cell is removed from the obtained culture to obtain the portion including *Clostridium botulinum* toxin expressed outside the cell, and the toxin is isolated from the portion (operation (b)). In the present operation, the toxin existing in the culture from which the cell is removed is isolated, and this operation may be performed using a conventional method in which a toxin included in a solution is isolated.

In an embodiment, operation (b) may include: removing the cell from the culture, adding an acid to the obtained culture to precipitate *Clostridium botulinum* toxin, and then isolating the precipitation (operation (b-1)); dissolving the isolated precipitation in a liquid medium and ultra-filtrating the resulting solution (operation (b-2)); and performing anion exchange chromatography on the ultra-filtered solution, i.e., the retentate.

In operation (b-1), the removing of the cell may be performed using at least one method selected from the group consisting of depth filtration and microfiltration. In addition, the precipitating of the toxin may be performed by adding an acid to the obtained culture to maintain the pH of the culture in the range of 3 to 4. The acid may be sulfuric acid, hydrochloric acid, acetic acid including glacial acetic acid, or the like.

In operation (b-2), the ultra-filtrating may be performed using a membrane having a molecular weight cutoff of 100 kDa or less. The dissolving of the isolated precipitation may be performed using a buffer, for example, a 10-50 mM citrate buffer (pH 5.0-6.0).

In operation (b-3), the anion exchange chromatography may use dextran, agarose-based diethylaminoethyl (DEAE), Q sepharose, or Q sephadex. Elution may be performed using only a citrate buffer instead of using NaCl.

In another embodiment, at least one of operations (a) and (b) may be performed using a pre-sterilized disposable container. In addition, in each operation, an inner space of the pre-sterilized disposable container in which a sample flows may not be in communication with an outer space of the pre-sterilized disposable container on which an operator works. For example, in a conventional open system, the removing of the cell from the culture may be performed by centrifugation or filtration. In this case, in a process of introducing the culture into a centrifugal separator or a filter and in a process of collecting the sample after centrifugation and filtration, the sample may be exposed to the outside. In addition, in the conventional open system, in a process of introducing the sample into a reactor, an ultra-filter, and a chromatography column used for precipitation, ultra-filtration, and chromatography, respectively, and in a process of collecting the sample after precipitation, ultra-filtration, and chromatography, the sample may be exposed to the outside. In the present invention, however, at least one of operations (a) and (b) is performed using the pre-sterilized disposable container, and thus the containers used in the at least one of operations (a) and (b), may be connected to each other so as not to contact with the outer space of the containers. Preferably, all the containers used in the operations (a) and (b) are connected to each other simultaneously or sequencially.

The present invention also provides a method of producing *Clostridium botulinum* toxin, the method including: introducing a culture media in a closed container including an inlet and an outlet and comprised of a flexible material, inoculating the culture media with *Clostridium botulinum*, and culturing the cell to express *Clostridium botulinum* toxin in the culture (operation (a)); and isolating *Clostridium botulinum* toxin from the obtained culture (operation (b)).

In operation (a), the culture media is introduced in the closed container including an inlet and an outlet and comprised of the flexible material, the culture media is inoculated with *Clostridium botulinum*, and the cell is cultured to express *Clostridium botulinum* toxin in the culture.

The closed container is well-known in the art related to animal cell culture and commercially available (for example, Cultibag™, manufactured by Wave Biotech). For example, the closed container may be a closed container disclosed in WO00/66706, but the present invention is not limited thereto. The closed container is pre-sterilized, and may be in a bag form, for example, in a plastic bag form.

The closed container may be stirred utilizing rocking motion. The culture media in the closed container mounted on a platform of a rocker may be stirred utilizing rocking motion. The rocker rocks the platform around an oscillation axis. The rocker is well-known in the art related to animal cell culture, and can be purchased as a part of Cultibag™ (Wave Biotech or Sartorius). The closed container is air-impermeable, and thus the inside thereof can be maintained in a condition that oxygen is not able to be provided from the outside, from when the culture media is introduced in the closed container and the culture media is inoculated with *Clostridium botulinum*, to when the culturing of the cell is completed.

Thus, the culturing may be performed without supplying nitrogen, without using a chemical material having oxygen removal activity (for example, sodium thioglycolate), or without adjustment of pH in order to maintain anaerobic conditions.

The media may be a conventional media used in culturing *Clostridium botulinum*. The media may include at least one of a media containing animal-derived components and a media containing plant-derived components, and may be preferably the media containing plant-derived components.

In an embodiment, the media containing plant-derived components may comprise phytone peptone, yeast extract, and glucose. In addition, the media containing plant-derived components may further comprise at least one component selected from the group consisting of vegetable tryptone, soytone, and sodium thioglycolate. In an embodiment, the media containing plant-derived components may be one selected from the group consisting of a media comprising glucose, yeast extract, and sodium thioglycolate, and further comprising at least two components selected from the group consisting of phytone peptone, vegetable tryptone, and soytone; a media comprising glucose, yeast extract, sodium thioglycolate, and not comprising phytone peptone, vegetable tryptone and soytone; and a media comprising glucose, yeast extract, phytone peptone, vegetable tryptone, and soytone. In another embodiment, the amounts of glucose, yeast extract, sodium thioglycolate, phytone peptone, vegetable tryptone, and soytone in each media described above may be 0.2 wt % to 2 wt %, 0.5 wt % to 3 wt %, 0.05 wt % to 2 wt %, 0.5 wt % to 2 wt %, 0.5 wt % to 2 wt %, and 0.5 wt % to 2 wt %, respectively, based on total weight of the media. In another embodiment, the media containing plant-derived components may be one selected from the group consisting of a media comprising glucose, yeast extract, sodium thioglycolate, and at least two components selected from the group consisting of phytone peptone, vegetable tryptone, and soytone, and water; a media comprising glucose, yeast extract, sodium thioglycolate, and water and not comprising phytone peptone, vegetable tryptone and soytone; and a media comprising glucose, yeast extract, phytone peptone, vegetable tryptone, soytone, and water. In this regard, the amounts of glucose, yeast extract, sodium thioglycolate, phytone peptone, vegetable tryptone, and soytone in each media described above are 0.2 wt % to 2 wt %, 0.5 wt % to 3 wt %, 0.05 wt % to 2 wt %, 0.5 wt % to 2 wt %, 0.5 wt % to 2 wt %, and 0.5 wt % to 2 wt %, respectively, based on the total weight of the media, and the rest of the media may comprise water.

The *Clostridium botulinum* toxin may be one selected from the group consisting of *botulinum* toxin A, B, C, D, E, F, and G, and preferably, *botulinum* toxin A.

When the media containing plant-derived components is used as described above, the toxin is secreted outside the cell. In this case, the toxin existing in the culture from which the cell is removed is isolated, and this isolation operation may be performed using a conventional method in which a toxin included in a solution is isolated.

In an embodiment, operation (b) may include: removing the cell from the culture, adding an acid to the obtained culture to precipitate *Clostridium botulinum* toxin, and then isolating the precipitation (operation (b-1)); dissolving the isolated precipitation in a liquid media and ultra-filtrating the resulting solution (operation (b-2)); and performing anion exchange chromatography on the ultra-filtered solution, i.e., the retentate.

In operation (b-1), the removing of the cell may be performed using at least one method selected from the group consisting of depth filtration and microfiltration. In addition, the precipitating of the toxin may be performed by adding an acid to the obtained culture to maintain the pH of the culture in the range of 3 to 4. The acid may be sulfuric acid, hydrochloric acid, acetic acid including glacial acetic acid, or the like.

In operation (b-2), the ultra-filtrating may be performed using a membrane having a molecular weight cutoff of 100 kDa or less. The dissolving of the isolated precipitation may be performed using a buffer, for example, a 10-50 mM citrate buffer (pH 5.0-6.0).

In operation (b-3), the anion exchange chromatography may use dextran, agarose-based diethylaminoethyl (DEAE), Q sepharose, or Q sephadex. Elution may be performed using only a citrate buffer instead of using NaCl.

In another embodiment, at least one of operations (a) and (b) may be performed using a pre-sterilized disposable container. In addition, in each operation, an inner space of the pre-sterilized disposable container in which a sample flows may not be in communication with an outer space of the pre-sterilized disposable container on which an operator works. For example, in a conventional open system, the removing of the cell from the culture may be performed by centrifugation or filtration. In this case, in a process of introducing the culture into a centrifugal separator or a filter and in a process of collecting the sample after centrifugation and filtration, the sample may be exposed to the outside. In addition, in the conventional open system, in a process of introducing the sample into a reactor, an ultra-filter, and a chromatography column used for precipitation, ultra-filtration, and chromatography, respectively, and in a process of collecting the sample after precipitation, ultra-filtration, and chromatography, the sample may be exposed to the outside. In the present invention, however, at least one of operations (a) and (b) is performed using the pre-sterilized disposable container, and thus the containers used in the at least one of operations (a) and (b) may be connected to each other so as not to contact with the outer space of the containers. Preferably, all the containers used in the operations (a) and (b) are connected to each other simultaneously or sequencially.

In the method of the present invention, *Clostridium botulinum* can produce *Clostridium botulinum* toxin, and can be, for example, Hall A of *Clostridium botulinum* type A (ATCC Deposition No. 3502).

*Clostridium botulinum* may be cultured under conventional culture conditions known in the art. The culturing may be performed at a temperature of 33 to 40° C. According to the method of the present invention, working environments around an incubator are the same as conventional working environments, and thus there is no need to make a separate sterile environment or no need for washing.

In the method of the present invention, each operation may be performed using a single use consumable. For example, a filtration system (single use depth filter and micro-filter) may be used as a centrifugal separation or a filtration system used in the removing of the cell, a single use system that is not in contact with the outside may be used as a precipitation system, and a single use ultrafiltration and chromatography system may be respectively used as an ultrafiltration and chromatography system. In addition, a single use sample transferring system may be used for transferring the sample. As such, the risk factors may be caused by contamination of *Clostridium botulinum* can be prevented.

Advantageous Effects

According to the method of present invention, *Clostridium botulinum* toxin was expressed outside the cell, and thus *Clostridium botulinum* toxin can be purified and produced easily and very simply. In addition, there is no need to purge nitrogen or use other equipment in order to make anaerobic conditions, and the fermentation can be performed using *Clostridium botulinum* strains even in a general working environment. In addition, according to the method of the present invention, the culturing of *Clostridium botulinum* and purifying of *Clostridium botulinum* toxin are performed in a closed system by using single use consumables, and thus the inside of the container including *Clostridium botulinum* and *Clostridium botulinum* toxin is not in contact with the outside of the container on which an operator works. Therefore, *Clostridium botulinum* toxin can be produced safely. In addition, even when a conventional fermentation and purification system that is complicatedly controlled is not used, *Clostridium botulinum* toxin with high purity can be produced.

BEST MODE

Hereinafter, the present invention will be described in further detail with reference to the following examples. These examples are for illustrative purposes only and are not intended to limit the scope of the present invention.

EXAMPLE 1

Confirmation of Media Composition that Makes a Large Amount of *Clostridium botulinum* Type A Toxin Expressed Outside the Cell in a Media Containing No Animal-Derived Components The fact that a large amount of *Clostridium botulinum* type A toxin was expressed outside the cell in a media containing no animal-derived components was confirmed using a variety of plant media.

The used media is shown in Table 1 below.

TABLE 1

| media | | 1 | 2 | 3 | 4 | 5 | 6 | 7 | 8 |
|---|---|---|---|---|---|---|---|---|---|
| Component and content (wt %) | Soytone 1% | ○ | | ○ | ○ | | | ○ | ○ |
| | Vegetable tryptone 1% | | ○ | | ○ | | ○ | | ○ |
| | Phytone peptone 1% | ○ | ○ | ○ | | ○ | | | ○ |
| | Sodium thioglycolate 0.05% | ○ | | | | | | | |
| | Yeast extract 1% | ○ | ○ | ○ | ○ | ○ | ○ | ○ | ○ |
| | glucose 0.5% | ○ | ○ | ○ | ○ | ○ | ○ | ○ | ○ |

In Table 1, the products manufactured by Beckton Dickinson and Fluka were respectively used as soytone and vegetable tryptone. In addition, products manufactured by Beckton Dickinson were used as phytone peptone and yeast extract, and a product manufactured by Merck was used as glucose. Media components of Table 1 were dissolved in water for injection (WFI), and the pH of the resulting solution was adjusted to 7.2 using NaOH.

In addition, 1 wt % of N-Z amine A (Sigma: animal derived), 2 wt % of Bacto Proteose Peptone #2 (pig derived), 1 wt % of Bacto Yeast Extract (BD), 1 wt % of glucose, and 0.05 wt % of sodium thioglycolate (Sigma) were dissolved in water and used as a control (hereinafter, referred to as 'animal derived medium' or 'control medium').

200 ml of each of the media of Table 1 and the control media was filtered through a sterilized single use microfiltration system (0.2 μm Sartorius 2, manufactured by Sartorius) so as to be injected into Cultibag™ (manufactured by Wave-Biotech, a single use fermentation bag). The microfiltration system, i.e., 0.2 μm of a sterile filter, was installed at the sample injection port of the bag, and 200 ml of the media was injected into the bag through the sterile filter. The injection of the media was performed using a peristaltic pump. Then, each media was inoculated with 1 ml of a seed inoculum including *Clostridium botulinum* type A with a concentration of $10^6 \sim 10^7$ cells/ml through a sample injection port. Cultibag™ is a disposable bioreactor that may use rocking motion in order to cause mixing. Cultibag™ is a bag including an inlet and outlet and a sample port and comprised of a flexible material, and the bag is air impermeable. In addition, the bag is equipped with a pump combined thereto, which is used for bag inflation and cell supply. When the bag is empty, the bag is in the form of a sheet that consists of two closely aligned layers of flexible materials, thereby has no substantial inner space volume. When a sample such as a medium or a cell solution is introduced through the inlet, a space between the two layers of the flexible materials is formed to accommodate the sample without any substantial introduction air. 1 L of the bag was used.

Culturing was performed such that 1 L of Cultibag™ including 200 ml of a seed culture was seed cultured at 37° C. for 12 to 24 hours while rocked at 10 rpm using a rocker unit included in Cultibag™, and the resultant was inoculated in the bag including 20 L of a main culture media through a sterilized single use connector (Kleenpack connector PALL) formed of a polycarbonate material by using a peristaltic pump, and then cultured for 48 to 72 hours, without additional operations to maintain an anaerobic conditions, since the inner space of Cultibag™ itself is maintained anaerobic to allow the growth of the *Clostridium botulinum*.

The seed culture media was injected to the bag through the sterile filter without a headspace so as to maintain anaerobic conditions. The seed culture was also injected using the same method used to inject the seed culture media without using the filter. In addition, the main culture was performed mounting the bag on a platform of the rocker unit of Cultibag™ and rocking the bag at 10 rpm at a temperature of 37° C. During the main culture, separate nitrogen purging in order to maintain the inside of the bag in anaerobic conditions was not performed, and additional reagents for anaerobic conditions were not used.

After the culturing was terminated, a sterile connector QDC connector (manufactured by Satorious) was connected to the sample port of the bag, and the culture was transferred to another disposable bag (flexible disposable bag) through the sterile connector. Then, a sterilized disposable depthfilter (Sartoclear or SupraCap, PALL) and microfilter (0.2 μm, Sartopore 2, Sartorius) were connected to the disposable container with the culture included therein, and the culture was filtered through the depthfilter and the microfilter to remove the cell. Then, the obtained supernatant was put in another disposable bag, without exposing the sample to the outside. 0.1 ml of a diluted sample in which the obtained supernatant was diluted with gelatin phosphate buffer (GPB) (0.2% of 30 mM gelatin-containing sodium phosphate, pH 6.2) at a predetermined ratio was injected to an peritoneal cavity of each 10 mice (ICR female mice, 4 weeks old), and a number of mice died three days after the injection was measured. The results are shown in Table 2 below.

TABLE 2

| media | Dilution ratio of culture supernatant with buffer and mortality (%) | | |
|---|---|---|---|
| | $10^{-3}$ | $10^{-4}$ | $10^{-5}$ |
| medium 1 | 100 | 100 | — |
| medium 2 | 100 | 100 | — |
| medium 3 | 100 | 100 | — |
| medium 4 | 100 | 100 | — |
| medium 5 | 100 | 100 | — |
| medium 6 | 100 | — | — |
| medium 7 | 100 | — | — |

TABLE 2-continued

| media | Dilution ratio of culture supernatant with buffer and mortality (%) | | |
|---|---|---|---|
| | $10^{-3}$ | $10^{-4}$ | $10^{-5}$ |
| medium 8 | 100 | 100 | — |
| Animal-derived medium | 100 | — | — |

As shown in Table 2, in the case of each of media 1 through 5 and medium 8, which is plant media, toxicity of the supernatant in which the cell is removed from the culture is about 10 times stronger than toxicity of the supernatant of the animal derived medium. Accordingly, when the media containing plant-derived components is used, it can be seen that a large amount of *Clostridium botulinum* type A toxin can be expressed outside the cell.

As shown in Table 2, taking into account that yeast extract and glucose are generally required components for growth of *Clostridium botulinum*, it is considered that phytone peptone, or soytone and vegetable tryptone plays a vital role in expressing *Clostridium botulinum* type A toxin outside the cell. Thus, it is better to use one component of phytone peptone in comparison with the combination of soytone and vegetable tryptone in terms of economical costs. Accordingly, most preferably, phytone peptone may be used in a combination with yeast extract, glucose and sodium thioglycolate.

As shown in Table 2, when the culturing is performed using the media containing plant-derived components (for example, media 1-5 and medium 8), a larger amount of *Clostridium botulinum* toxin protein exists in the culture supernatant, as compared to the animal-derived medium. Thus, the inventors of the present application surprisingly found that when the media containing plant-derived components was used, *Clostridium botulinum* toxin protein was expressed outside the cell, and thus there was no need for complex purification processes.

The results of Table 2 were the same as SDS-PAGE results obtained using the culture from which the cell was removed as a sample (data is not shown).

As described above, it was confirmed that in Example 1, media compositions that can express a larger amount of *Clostridium botulinum* type A toxin outside the cell by using the media containing plant-derived components, as compared to the animal-derived medium, were obtained.

Hereinafter, a method of producing *Clostridium botulinum* type A toxin from the culture from which the cell is removed will be described more fully.

*Clostridium botulinum* type strains are strict anaerobes, and not in anaerobic atmospheric conditions, the strains do not grow, and also do not express toxic products. In the prior art, to make the anaerobic atmospheric conditions, the following three methods are used alone or in the combination: first, a method of using sterilization, second, a method of using a chemical material (for example, sodium thioglycolate), and third, a method of maintaining oxygen-free atmospheric conditions by nitrogen purging. However, these methods require equipment, and residues may also occur. These may act as a high risk factor in building a good manufacturing practice (GMP) and biosafety level (BSL) 3 laboratory. However, in the present invention, when at least one of the media containing plant-derived components and the disposable bioreactor is used, contact with oxygen can be prevented even when the three methods are not used (refer to medium 5). In addition, there is no problem in producing botulinum toxin protein, which is a peculiar characteristic of *Clostridium botulinum* strains.

In addition, in the prior art described above, a process of compulsorily reducing pH is needed for producing toxin protein, whereas, in the present invention, a large amount of toxin protein can be expressed outside the cell and produced through only a simple culturing in a closed flexible bag system without using such a process of compulsorily reducing pH.

EXAMPLE 2

This embodiment was performed in the same manner as in Example 1, except that rocking was not performed in the culturing using Cultibag™.

As a result, there was no substantial difference between the amount of produced toxin and the amount of toxin of Example 1.

EXAMPLE 3

Isolation of *Clostridium botulinum* Type A Toxin from a Supernatant of Culture Using a Media Containing Plant-Derived Components

*Clostridium botulinum* was cultured using the medium 5 of Example 1 or 2, and *Clostridium botulinum* type A toxin was isolated from a supernatant from which the cell was removed. The culturing conditions and time and the cell removal process were the same as those in Example 1.

0.1 N sulfuric acid was added to a bag including 20 L of a culture supernatant to adjust the pH of the resulting solution to be in the range of 3.0 to 4.5, and as a result, toxin protein was precipitated. This process was performed in a disposable sample bag not in contact with the outside.

Then, when the precipitation was completed, the resulting solution was filtered through a sterilized disposable filtration system (disposable slice 200 0.2 µm filter, manufactured by Sartorius) not in contact with the outside to remove the supernatant, and the precipitation was collected in a disposable sample bag. 10 L of WFI was added to the collected precipitation to wash the sulfuric acid, and a sterilized disposable microfiltration system (disposable slice 200 0.2 µm filter) was connected to the disposable sample bag and the resulting solution was filtered through the system to remove the supernatant. As a result, the precipitation was collected into a disposable bag.

10 L of a 25 mM citrate buffer (pH 5.5) was added to the collected precipitation to re-dissolve toxin protein existing in the precipitation. This process was also performed in a disposable bag not in contact with the outside. A sterilized disposable filtration system (0.2 µm, ULTA Cap HC, GE, USA) was connected to the bag including the redissolved toxin protein and filtration was performed on the toxin protein through the system not in contact with the outside. As a result, the supernatant was collected in a sterilized disposable bag and insoluble impurities were removed.

A sterilized disposable ultrafiltration membrane (disposable slice 200 100 kDa, manufactured by Sartorius) having a molecular weight cutoff of 100 kDa was connected to the bag including the sample from which the insoluble impurities were removed. Then, the sample was filtered with no contact with the outside to be enriched, and a buffer exchange was performed on the enriched resultant by using a 25 mM citrate buffer (pH 5.5). Even in this process, toxin protein contacts an inner surface of the sterilized container, and is not in contact with the outside.

Then, a disposable DEAE chromatography system (DEAE BPG Column™: GE Healthcare) and a sterilized disposable membrane chromatography system (Sartobind D™: Sartorius) were sequentially connected to the bag including the sample after the enrichment and buffer exchange were completed. Then, DEAE anion exchange chromatography and membrane chromatography were performed on the sample not in contact with the outside. The disposable chromatography system was pre-washed. After the sample was loaded on the system, the *Clostridium botulinum* type A toxin protein in the sample was not bound to a column while other impurities were bound to the column, and thus a fraction flowing out of the system was collected. As a result, impurities were removed with no contact with the outside, and *Clostridium botulinum* type A toxin protein with high purity was collected. In addition, the yield of *Clostridium botulinum* type A toxin purified in the media containing plant-derived components was about 5-10 times higher than the yield of the toxin purified in the animal-derived medium used as a control.

The sample obtained in each operation was analyzed through SDS-PAGE and SEC-HPLC. As a result of final purification, *Clostridium botulinum* type A toxin having a purity of 95% or greater was obtained. Thus, it was confirmed that *Clostridium botulinum* type A toxin could be produced from the culture from which the cell was removed in a high purity and high yield.

As a result of SDS-PAGE and SEC-HPLC, it can be seen that *Clostridium botulinum* type A toxin is a complex of 8 proteins, and can be produced in a high purity and high yield by using the method of the present invention (data not shown).

While the present invention has been particularly shown and described with reference to exemplary embodiments thereof, it will be understood by one of ordinary skill in the art that various changes in form and details may be made therein without departing from the spirit and scope of the present invention as defined by the following claims.

INDUSTRIAL APPLICABILITY

According to the method of present invention, *Clostridium botulinum* toxin was expressed outside the cell, and thus *Clostridium botulinum* toxin can be purified and produced easily and very simply.

The invention claimed is:
1. A method of producing *Clostridium botulinum* toxin, the method comprising:
(a) introducing a culture medium in a closed container comprising an inlet and an outlet and comprised of a flexible material, inoculating the culture medium with *Clostridium botulinum*, and culturing the cell to express *Clostridium botulinum* toxin in the culture; and
(b) isolating *Clostridium botulinum* toxin from the obtained culture in a second container,
wherein culturing is performed under anaerobic conditions without using a chemical material having oxygen removal activity in order to maintain said anaerobic conditions, and
wherein at least one of operations (a) and (b) is performed using a pre-sterilized disposable container, and in each operation, the containers used in operations (a) and (b) are connected to each other, such that the contents of the containers do not contact the outer space of the containers.

2. The method of claim 1, wherein the closed container is in a bag form.

3. The method of claim 1, wherein the closed container is stirred utilizing rocking motion.

4. The method of claim 1, wherein the closed container is air impermeable.

5. The method of claim 1, wherein the culturing is performed without supplying nitrogen, or without adjustment of pH in order to maintain anaerobic conditions.

6. The method of claim 1, wherein the media is one selected from the group consisting of a media comprising glucose, yeast extract, and phytone peptone; a media comprising glucose, yeast extract, phytone peptone, and vegetable tryptone; a media comprising glucose, yeast extract, phytone peptone, and soytone; a media comprising glucose, yeast extract, soytone, and vegetable tryptone; and a media comprising glucose, yeast extract, phytone peptone, vegetable tryptone, and soytone.

7. The method of claim 6, wherein the amounts of glucose, yeast extract, phytone peptone, vegetable tryptone, and soytone in each media are 0.2 wt % to 2 wt %, 0.5 wt % to 3 wt %, 0.5 wt % to 2 wt %, 0.5 wt % to 2 wt %, and 0.5 wt % to 2 wt %, respectively, based on total weight of the media.

8. The method of claim 1, wherein the *Clostridium botulinum* toxin is one selected from the group consisting of *botulinum* toxin A, B, C, D, E, F, and G.

9. The method of claim 1, wherein operation (b) comprises:
(b-1) removing the cell from the culture, adding an acid to the obtained culture to precipitate *Clostridium botulinum* toxin, and then isolating the precipitation;
(b-2) dissolving the isolated precipitation in a liquid medium and ultra-filtrating the resulting solution; and
(b-3) performing anion exchange chromatography on the ultra-filtered solution.

10. The method of claim 9, wherein in operation (b-1), the removing of the cell is performed using at least one method selected from the group consisting of depth filtration and microfiltration and the precipitating of the toxin is performed by adding an acid to the obtained culture to maintain the pH of the culture in the range of 3 to 4, and in operation (b-2), the ultrafiltration is performed using a membrane having a molecular weight cutoff of 100 kDa or less.

* * * * *